United States Patent [19]

Ducheyne et al.

[11] Patent Number: 5,658,332
[45] Date of Patent: Aug. 19, 1997

[54] BIOACTIVE GRANULES FOR BONE TISSUE FORMATION

[75] Inventors: Paul Ducheyne, Rosemont; D. Scott Metsger, Downingtown, both of Pa.; Evert Schepers, Leuven, Belgium

[73] Assignee: Orthovita, Inc., Malvern, Pa.

[21] Appl. No.: 268,510

[22] Filed: Jun. 30, 1994

[51] Int. Cl.$^6$ ....................................................... A61F 2/28
[52] U.S. Cl. ......................... 623/16; 606/76; 433/201.1
[58] Field of Search .............................. 623/16; 606/76; 523/115; 433/201.1

[56] References Cited

U.S. PATENT DOCUMENTS

| | | | |
|---|---|---|---|
| 3,905,047 | 9/1975 | Long | 3/1.9 |
| 3,981,736 | 9/1976 | Broemer et al. | 106/39.6 |
| 4,131,597 | 12/1978 | Bluethgen et al. | 260/42.18 |
| 4,159,358 | 6/1979 | Hench et al. | 427/318 |
| 4,239,113 | 12/1980 | Gross et al. | 206/568 |
| 4,563,350 | 1/1986 | Nathan et al. | 424/95 |
| 4,608,350 | 8/1986 | Howard | 501/20 |
| 4,786,555 | 11/1988 | Howard | 428/403 |
| 4,851,046 | 7/1989 | Low et al. | 106/35 |
| 5,141,511 | 8/1992 | Bauer | 623/16 |
| 5,204,106 | 4/1993 | Schepers et al. | 424/423 |

FOREIGN PATENT DOCUMENTS

| | | |
|---|---|---|
| 0112319 | 11/1983 | European Pat. Off. . |
| 0145210 | 10/1984 | European Pat. Off. . |
| 0206726 | 6/1986 | European Pat. Off. . |
| 0263489 | 10/1987 | European Pat. Off. . |
| 382047 | 8/1990 | European Pat. Off. . |
| 2606282 | 12/1986 | France . |
| 3306648A1 | 2/1983 | Netherlands . |

OTHER PUBLICATIONS

Wilson, J. et al., "Bioactive Materials for Periodontal Treatment: A Comparative Study", *Biomaterials and Clinical Applications* 1987, pp. 223–228.

Gatti et al., "Glass Corrosion Layers on Bioactive Glass Granules of Uniform Size Affect Cellular Function", *Bioceramics* 6:395–400 (1993).

Gatti et al., "In-Vivo Reactions In Some Bioactive Glasses And Glass–Ceramics Granules", *Cells and Materials* 3:283–291 (1993).

Gatti and Zaffe, "Short–Term Behaviour Of Two Similar Active Glasses Used As Granules In The Repair Of Bone Defects", *Biomaterials* 12:497–504 (1991).

Gatti and Zaffe, "Long–Term Behaviour of Active Glasses in Sheep Mandibular Bone", *Biomaterials* 12:345–350 (1991).

Hench et al., "Bonding Mechanisms at the Interface of Ceramic Prosthetic Materials", *J. Biomed. Mater. Res. Symp.*, 2:117–141 (1971).

Neo et al., "A Comparative Study of Ultrastructures of the Interfaces Between Four Kinds of Surface–Active Ceramic and Bone", *Journal of Biomedical Materials Research* 26:1419–1432 (1992).

Schepers et al., "Bioactive Glass Particles of Narrow Size Range: a new material for the repair of bone defects," *Implant Dent.* 2(3):151–6 (1993).

Schepers et al., "Bioactive Glass Particulate material As A Filler For Bone Lesions", *J. Oral Rehabil.* 18(5):439–52 (1991).

Schepers et al., "Clinical Application of Bioactive Glass Granules of Narrow Size Range on Dental Osseous Lesions", *Bioceramics* pp. 361–364 (1993).

(List continued on next page.)

*Primary Examiner*—Paul B. Prebilic
*Attorney, Agent, or Firm*—Woodcock Washburn Kurtz Mackiewicz & Norris

[57] ABSTRACT

Methods for forming osseous tissue in defects in sites in the appendicular skeleton or sites exhibiting reduced metabolic state using bioactive glass granules containing 40 to 58% $SiO_2$, 10 to 30% NaO, 10 to 30% CaO, and 0 to 10% $P_2O_5$, and in the size range of from 200 to 300 micrometers, are described.

9 Claims, 2 Drawing Sheets

OTHER PUBLICATIONS

Schepers and Ducheyne, "The Application of Bioactive Glass Particles of Narrow Size Range as a Filler Marterial for Bone Lesions: a 24 month Animal Experiment", *Bioceramics* pp. 401–404 (1993).

Schepers and Pinruethai, "A Comparative Study of Bioactive Glass and Porous Hydroxylapatite Particles in Periodontal Bone Lesions", *Bioceramics* pp. 113–116.

Tortora, G.J., (Ed.), "*Principles of Human Anatomy*", pp. 92–204, Harper & Row, New York, (1983).

Wilson and Low, "Bioactive Ceramics For Periodontal Treatment: Comparative Studies In the Patus Monkey.", *J. Applied Biomaterials* 3:123–30 (1992).

BIOACTIVE GRANULES FOR BONE TISSUE FORMATION

TECHNICAL FIELD

The present invention is related to implant materials of bioactive glass.

BACKGROUND OF THE INVENTION

The biocompatability of bioactive glasses, as evidenced by tight apposition of hard tissue to implanted glassy particles, has been demonstrated continuously since 1971. Specifically, the composition of one such bioactive glass, 45S5 Bioglass®, was originally reported by Hench et al., *J. Biomed. Mater. Res. Symp.*, 2: 117–141 (1971). The nature of the bone tissue/glass interface has been discussed in terms of the formation of a reactive region on the surface of the glass. It has been established that ionic exchange between the extracellular fluid and the glass at the surface transforms the silica constituent of the glass to a gel while increasing the pH of the surrounding local environment. Simultaneously, a thin layer of calcium phosphate forms on the outer surface of the glass mediated through cellular activity. Bone grows by apposition onto bioactive glass placed adjacent to bony surfaces and new bone may be conducted subsequently, over short distances. In the instance in which the bioactive glass is in the form of granules, new bone can be conducted from granule to granule.

Granules of bioactive glass have been described previously. U.S. Pat. No. 4,239,113 describes a composition for the preparation of bone cement. The cement has an inorganic portion which comprises between 15 and 75% by weight of the cement. The inorganic portion further contains bio-active glass ceramic powder having a particle size of 10–200 micrometers in a portion of 90–99% by weight and between 1–10% vitreous mineral fibers by weight. The bone cement composition further contains an admixture of methylmethacrylate copolymers and methylmethacrylate, a curing catalyst, and, preferably, an accelator.

U.S. Pat. No. 4,851,046 describes compositions containing particles of 45S5 Bioglass® of various size ranges for use in periodontal applications. It was asserted that particles of a larger size range might produce a more clinically desirable mixture. A particle size range of 90–710 micrometers was specifically described as being the most effective. The glass powders mixed well with blood and formed a cohesive mix, which also stopped the bleeding.

U.S. Pat. No. 5,204,106, issued to Schepers, et al. on Apr. 20, 1993 (incorporated herein by reference), discloses that particles of bioactive glass having the composition of 45S5 within the narrow size range of 280 to 425 micrometers (μm) elicit a distinctively altered biologic response from that described previously. Particles within this specific size range were implanted into the jaw bone of young adult dogs and became disintegrated from the inside, i.e. excavated, disappeared, and were progressively and rapidly replaced by osseous tissue rather than by fibrous tissue. It is disclosed that, as the particles disintegrate, the interior constitutes a highly protected medium, which makes it possible to create and maintain conditions favorable to the differentiation of mesenchymal cells into osteoblasts. When 45S5 bioactive glass particles outside the specified size range were implanted, however, excavation was not observed. With larger particles (i.e., 425–850 μm), there was no central disintegration with glass resorption or dissolving and substitution by osseous tissue. External growth of osseous tissue by osteoconduction from the cavity wall was observed, but the particles in the center of the cavity were surrounded by fibrous tissue. With smaller particles (i.e. 212–300 μm), osteoconduction was observed from the cavity wall, but, again, the particles in the center were surrounded by fibrous tissue, prior to disappearing under the action of phagocytic cells.

The particles disclosed in Schepers et al. have also been used in orthopaedic sites with success. Specifically, particles in the range of 300 to 355 μm have been implanted into the ankle of a patient to fill screw holes upon removal of a bone plate. X-ray follow-up revealed that the granules stimulated bone tissue formation.

Notably, the bone formation observed in Schepers et al. occurs throughout the entire defect through osteogenesis by osteostimulation, assisted by osteoconduction due to the calcium phosphate layer which is formed prior to the central, cellularly mediated disintegration. Upon central disintegration, the bioactive glass particles are fully transformed into calcium phosphate. The composition and size of the preferred granules in the Schepers et al. patent are such that the particles are gradually transformed as the defect site becomes vascularized and populated with bone tissueforming cells. The smaller particles reacted too rapidly, generating an acute inflammatory response, and thereby impeding bone tissue formation.

The material described in the Schepers et al. patent is suitable for many instances of defect repair where particles of increased bone tissue forming capability are not necessary. However, there remains a need for a material with greater reactivity in some applications of defect repair. Those instances are described in more detail below.

SUMMARY OF THE INVENTION

It was desired to extend the range of useful particle sizes for bioactive granules. Smaller particles hasten bone repair by providing more nuclei for bone tissue formation. In addition, if the corrosion and resorption reactions could be controlled such that there is no acute inflammatory response reactions elicited interfering with bone tissue formation, a faster repair of the defect site will be achieved. Recognizing that the jaw is in an area of enhanced fluid flow, that is in a region above the neck, it was postulated that the abundance of interstitial fluids and the enriched blood supply in such areas, in conjunction with the increased bioactivity of smaller particles, contributed to the imperfect results previously observed for the smaller granules. Furthermore, it was reasoned that the rigorous metabolic rate in the young adult dogs contributed to the heightened inflammatory response previously seen with the small particles.

In one aspect, the present invention relates to a method for forming osseous tissue in an orthopaedic site in the appendicular skeleton comprising implanting particles of bioactive glass in the size range of from about 200 to about 300 micrometers. The appendicular skeleton as described in *Principles of Human Anatomy*, Gerard J. Tortora, ed., pp 92–204, Harper & Row, New York, (1983) (incorporated herein by reference) includes the shoulder girdle—clavicle and scapula; upper extremities—humerus, ulna, radius, carpals, metacarpals, and phalanges; pelvic girdle—pelvic bone; and lower extremities—femur, fibula, tibia, patella, tarsals, metatarsals and phalanges. As will be understood by one skilled in the art, the appendicular skeleton does not generally experience the enhanced fluid flow observed in the cranio-facial skeleton. The term "appendicular skeleton" as used herein includes comparable regions of non-human animals.

In another aspect, the present invention relates to a method for forming osseous tissue in any bone tissue site of reduced metabolic state comprising implanting particles of bioactive glass in the size range of from about 200 to about 300 micrometers. Metabolic states are influenced by the age and genetic disposition of a subject. For example, a "reduced metabolic state" is observed in subjects with osteoporosis. Reduced metabolic states are also generally observed in elderly persons. Elderly as defined herein includes persons aged 60 and over, although there can be exceptions. There will also be other situations in which a reduced metabolic state is exhibited, which are encompassed by the present invention. Although certain diagnostic tests can be performed to provide evidence of a reduced metabolic state, the assessment is not completely empirical. The assessment, however, can be readily made by those skilled in the art. It will be appreciated that the method according to the invention can be used in any osseous location in a reduced metabolic state.

It is also contemplated that there are sites of intermediate fluid flow and metabolism, or an evolution of such sites, for which having an implant material according to the invention is desirable. Further, regions generally considered to have the characteristics of enhanced fluid flow and metabolism may not exhibit these characteristics under certain circumstances, or in certain disease states. In that instance, implantation of the granules according to the present invention would be appropriate in such a region, even if it be in the cranio-facial area as described above.

Osseous defects contemplated include, but are not limited to, the following: cystic defect repairs, benign and malignant tumor sites upon resection, bone loss, fracture repair sites including delayed- or non-union sites, joint repair sites, osteoporosis-related defects, and periodontal defects.

The compositions and methods described herein can be used in veterinary and human application.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
FIG. 1 depicts excavation observed with granules of 45S5 glass.

The method according to the invention involves the implantation of granules of bioactive glass in the size range of from about 200 to about 300 micrometers. The bioactive glass granules contain oxides of silicon, sodium, calcium, and phosphorous in the following percentages by weight: 40 to 58% $SiO_2$, 10 to 30% $Na_2O$, 10 to 30% $CaO$, and 0 to 10% $P_2O_5$ or, more specifically, 42 to 54% $SiO_2$, 15 to 27% $Na_2O$, 15 to 27% $CaO$, and 3 to 8% $P_2O_5$. In a preferred embodiment, the composition of the bioactive glass granules is 45% $SiO_2$, 24.5% $Na_2O$, 24.5% $CaO$, and 6% $P_2O_5$. In another preferred embodiment, the composition of the bioactive glass granules is 52% $SiO_2$, 21% $Na_2O$, 21% $CaO$, and 6% $P_2O_5$.

In previous studies using particles of 45S5 bioactive glass ranging in size from 212 to 300 micrometers, excavation was not realized. "Excavation" is defined as the formation of a central cavity through the interior of the particle at the time of full reaction of the particle which includes gelation and calcium phosphate layer formation. Subsequently, osteoprogenitor cells, including mesenchymal cells, penetrate into the cavity and differentiate into bone forming cells. Thus, osseous tissue is formed by osteostimulation from within the defect. Excavation is evident by the observation of cells within a particle having a defined rim.

One reason excavation may not have been realized previously with smaller particles is the abundant corrosion reaction of such particles in a site of enhanced fluid flow and vigorous metabolic state. This led to an acute inflammatory response Generally, the corrosion reaction proceeds at increased rates with increased surface area and, concomitantly, decreased particle diameter. Accordingly, it was thought that particles of bioactive glass in the size range of about 200 to about 300 micrometers may be too reactive in some regions of enhanced fluid flow. It was expected that, even in sites not having enhanced fluid flow, some modification of the composition would be required to observe excavation with smaller particles.

Granules of bioactive glass particles in the size range of from about 200 to about 300 microns having four different glass compositions were specifically prepared. The granules were prepared using the melt-derived and grinding process described previously in U.S. Pat. No. 5,204,106, the disclosure of which is incorporated herein by reference. However, it is expected that granules prepared by other processes may also be suitable.

The four different compositions utilized are listed below in Table I. The first composition represents that of bioactive glass designated as 45S5. GI through GIII represent modifications of the glass composition.

TABLE I

Composition of Bioactive Glass Particles

| Group | Si, wt % | Ca, wt % | Na, wt % | P, wt % | Designation |
| --- | --- | --- | --- | --- | --- |
| I | 45 | 24.5 | 24.5 | 6 | 45S5 |
| II | 52 | 21 | 21 | 6 | GI |
| III | 52 | 24 | 24 | 0 | GII |
| IV | 60 | 17 | 17 | 6 | GIII |

Implantation was in defects created in the ilium of rabbits. The ilium has limited cancellous bone and, therefore, defects do not repair quickly through growth of new bone. Further, the ilium is not in a site of enhanced fluid flow. Thus, the ilium was chosen as the site for implantation. Rabbits were chosen as an accepted animal model for studying the response to materials for both veterinary and human use.

Unexpectedly, it was found that particles having the 45S5 composition in the size range of 200 to 300 micrometers were being excavated after four weeks of implantation. Extensive osteoconduction with direct bone bonding to particles was observed in association with excavation of the particles. Evidence of compositional changes and excavation were also noted with the GI composition; large amounts of bone are also found throughout these defects.

EXAMPLE 1

Rabbits were implanted with granules of 200 to 300 micrometers having the compositions listed in Table I. Each rabbit was implanted with all four compositions. Two circular defects of three millimeters (mm) in diameter were placed on 15 mm centers in each ilia of New Zealand white rabbits. The defects were enlarged sequentially in three stages to a final diameter of eight mm and filled with glass granules (200–300 μm) having one of the compositions shown in Table I. Each defect was implanted with material of a singular composition. Placement was random. The rabbits were sacrificed four weeks after implantation for histological examination of the repair.

Block sections of the ilia were excised and embedded in polymethylmethacrylate. Five serial sections were obtained from each defect, near a diameter. Three sections were stained—one each with trichrome, which is generally used for observing cellular detail; Giemsa, which is used to contrast bone and fibrous tissue; and Paragon, which is used contrast bone and fibrous tissue and glass, and for cellular detail.

The histological observations from three rabbits are presented in Table II below. In the table, "RC", "RA", "LC", and "LA" represent the right and left, caudal and cephalic defects, respectively. "Caudal" refers to the defect positioned more toward the rear of the animal. "Cephalic" refers to the defect positioned more toward the head. The "Group" numbers correspond to those listed in Table I. "Excavation" was described previously. "Composition Changes" are those changes in coloration and hue of the particles observable upon staining. This is indicative of glass corrosion reactions leading to changes in chemical composition of the granule material. "Bone Fill" is defined in terms of repair of the individual defect. This may occur as a normal reparative process and, therefore, is not necessarily due to the use of the material per se. It does not relate to comparison with a control. "Macrophage Disintegration" refers to the observation of phagocytosing cells in close proximity with the outside of the granules: The scalloping appearance of some of the granules is caused by these cells. The scale is as follows: an "ND" indicates that no observation was attempted, a "−" indicates that the item was not observed, a "+" indicates that the item occurred, a "++" indicates that much of the item was observed, a "+++" indicates that the item was observed extensively.

In the case of the 45S5 composition of the specified size range, particles fully reacted with visible evidence of excavation at the core. This is depicted in FIG. 1. FIG. 1 represents tissue from Rabbit 12RA stained with trichrome and viewed at 100× magnification. Excavation is indicated by the arrows.

Figure 2:
FIG. 2 depicts excavation observed with granules of GI glass composition.

The reaction layer associated with GI granules extended approximately one-half of the way into the centers at four weeks; particles were not fully reacted at this time period, but excavation was in progress. This is depicted in FIG. 2. FIG. 2 represents tissue from rabbit 9LA stained with trichrome and viewed at 100× magnification. Region of excavation in progress is indicated by the arrow.

Particles of the GII composition had a very thin reaction layer that exhibited a moth-eaten appearance due to macrophagic resorption of the surface in selected areas. The use of GIII particles resulted in an abundance of macrophages in close proximity to the granules and an absence of major composition changes of the surface. In the case of GII and GIII materials, less bone apposition to the glass granules was observed.

The foregoing is meant to illustrate the invention, and not limit it in any way. Those skilled in the art will recognize that modifications can be made which are within the spirit and scope of the invention as defined in the appended claims.

TABLE II

Summary of Histological Observations at Four Weeks

| Rbt | Position | Group | Excavation | Composition Changes | Bone Fill | Macrophage Distingegration |
|---|---|---|---|---|---|---|
| 9 | RC | I | + | +++ | + | − |
|   | LA | II | + | ++ | ++ | − |
|   | LC | III | − | + | ++ | − |
|   | RA | IV | − | − | + | ++ |
| 12 | RA | I | +++ | +++ | +++ | − |
|   | LC | II | + | ++ | + | − |
|   | RC | III | − | + | ND | + |
|   | LA | IV | − | − | + | ND |
| 14 | LC | I | + | +++ | ++ | − |
|   | RC | II | + | ++ | + | − |
|   | LA | III | − | + | + | + |
|   | RA | IV | − | − | ND | + |

What is claimed is:

1. A method for forming osseous tissue throughout an orthopaedic defect in a site located in the appendicular skeleton comprising
   a) filling said site with particles consisting essentially of:
      from about 40 to about 58% $SiO_2$,
      from about 10 to about 30% $Na_2O$,
      from about 10 to about 30% CaO and
      up to about 10% $P_2O_5$, by weight in a size range of from about 200 to about 300 micrometers; and
   b) whereby said particles are to be transformed, and individual particles become excavated, forming a calcium phosphate outer layer with a central cavity into which osteoprogenitor cells penetrate and differentiate into bone forming cells which, in association with osteoconduction, results in said osseous tissue formation.

2. The method of claim 1 wherein said particles consist essentially of:
   from about 42 to about 54% $SiO_2$,
   from about 15 to about 27% $Na_2O$,
   from about 15 to about 27% CaO and
   from about 3 to about 8% $P_2O_5$, by weight.

3. The method of claim 1 wherein said particles consist essentially of about 45% $SiO_2$, about 24.5% $Na_2O$, about 24.5% CaO, and about 6% $P_2O_5$, by weight.

4. The method of claim 1 wherein said particles consist essentially of about 52% $SiO_2$, about 21% $Na_2O$, about 21% CaO, and about 6% $P_2O_5$, by weight.

5. A method for forming osseous tissue throughout an osseous defect in a site of reduced metabolic state comprising
   a) filling said site with particles consisting essentially of:
      from about 40 to about 58% $SiO_2$,
      from about 10 to about 30% $Na_2O$,
      from about 10 to about 30% CaO and
      up to about 10% $P_2O_5$, by weight in a size range of from about 200 to about 300 micrometers; and
   b) whereby said particles are to be transformed, and individual particles become excavated, forming a calcium phosphate outer layer with a central cavity into which osteoprogenitor cells penetrate and differentiate into bone forming cells which, in association with osteoconduction, results in said osseous tissue formation.

6. The method of claim 5 wherein said particles consist essentially of:
   from about 42 to about 54% $SiO_2$, from about 15 to about 27% $Na_2O$, from about 15 to about 27% CaO and from about 3 to about 8% $P_2O_5$, by weight.

7. The method of claim 5 wherein said particles consist essentially of about 45% $SiO_2$, about 24.5% $Na_2O$, about 24.5% CaO, and about 6% $P_2O_5$, by weight.

8. The method of claim 5 wherein said particles consist essentially of 52% $SiO_2$, about 21% $Na_2O$, about 21% CaO, and about 6% $P_2O_5$, by weight.

9. A method for forming osseous tissue throughout an osseous defect in a site of reduced metabolic state in an osteoporotic subject comprising a) filling said site with particles consisting essentially of:
from about 40 to about 58% $SiO_2$,
from about 10 to about 30% $Na_2O$
from about 10 to about 30% CaO and
up to about 10% $P_2O_5$, by weight in a size range of from about 200 to about 300 micrometers; and b) whereby said particles are to be transformed, and individual particles become excavated, forming a calcium phosphate outer layer with a central cavity into which osteoprogenitor cells penetrate and differentiate into bone forming cells which, in association with osteoconduction, results in said osseous tissue formation.

* * * * *